United States Patent [19]

Trebosc et al.

[11] Patent Number: 5,030,451
[45] Date of Patent: Jul. 9, 1991

[54] TOPICAL SLENDERIZING FORMULATION CONTAINING CAFEINE CARBOXYLIC ACID DERIVATIVES NEUTRALIZED BY ORGANIC BASES, PREPARATION THEREOF, AND THEIR USE IN THE TREATMENT OF CELLULITE

[75] Inventors: Marie-Thérése Trebosc, Castres; Gilbert Mouzin, Toulouse; Henri Cousse, Castres, all of France

[73] Assignee: Pierre Fabre S.A., Castres, Cedex, France

[21] Appl. No.: 442,807

[22] Filed: Nov. 29, 1989

[30] Foreign Application Priority Data

Nov. 29, 1988 [FR] France .................................. 88 15575

[51] Int. Cl.$^5$ ............................................. A61K 31/00
[52] U.S. Cl. .................... 424/401; 424/489; 424/63; 424/69; 514/359; 514/387
[58] Field of Search ................ 424/489, 490, 63, 69, 424/484; 514/387, 385, 389

[56] References Cited

U.S. PATENT DOCUMENTS 4,191,748 3/1980 Holzmann ............................ 424/94
4,288,433 9/1981 Noulbanis et al. .................. 424/432
4,938,962 7/1990 Trebosc et al. ..................... 424/439

*Primary Examiner*—Thurman Page
*Assistant Examiner*—Louis A. Piccone
*Attorney, Agent, or Firm*—Gordon W. Hueschen

[57] ABSTRACT

The present invention relates to topical compositions containing caffeine carboxylates with organic bases, which are useful as slenderizing agents and in the treatment of cellulitis, as well as their preparation.

The heterogeneous topical compositions of the invention contain, as active principle, a caffeine carboxylic acid which has been salified with a cosmetologically-acceptable organic base, the active principle preferably being present in the form of microparticles or microgranules suspended in a hydroalcoholic gel.

16 Claims, No Drawings

TOPICAL SLENDERIZING FORMULATION CONTAINING CAFEINE CARBOXYLIC ACID DERIVATIVES NEUTRALIZED BY ORGANIC BASES, PREPARATION THEREOF, AND THEIR USE IN THE TREATMENT OF CELLULITE

BACKGROUND OF INVENTION AND PRIOR ART

The present invention, which originates from the PIERRE FABRE Dermatological and Cosmetological Center, relates to new cosmetic formulations, in which a novel slenderizing active principle is present in solution or in a heterogeneous suspension within a hydroalcoholic gel in the form of microgranules or microparticles, which are useful in the treatment of cellulite.

The active principle of the present invention consists essentially of an organic salt of caffeine carboxylic acid, advantageously in combination with Vitamin E or caffeine or a derivative of either or both of said compounds.

The active principle of the novel formulations of the present invention is a salt of caffeine carboxylic acid, with an organic base, having the following Formula I:

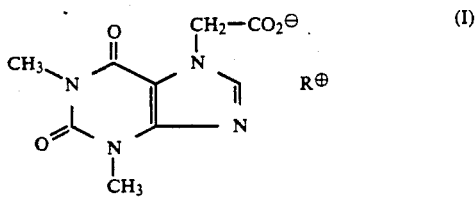

wherein:

R+ represents a protonized organic base and preferably one of the following organic bases:

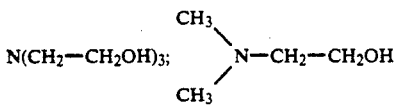

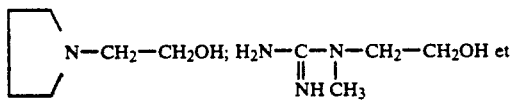

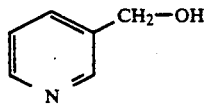

The active principles employed according to the present invention have been subjected to pharmacokinetic tests using caffeine carboxylic acid labelled with carbon 14.

The results of this study show that the rate of transcutaneous passage is faster when the salifying agent is an organic base, especially in the case of 3-nicotinol caffeine carboxylate which confirms the superiority of these active agents in the treatment of cellulite. The active principles of the present invention can also be advantageously employed in combination with caffeine, Vitamin E, or one of their derivatives.

OBJECTS OF THE INVENTION

It is an object of the present invention to provide new and improved topical compositions or formulations for use in slenderizing and in the treatment of cellulitis, such compositions which contain at least one novel and long-acting principle which is a topically- and cosmetically- or cosmetologically-acceptable caffeine carboxylate formed between caffeine carboxylic acid and a cosmetologically-acceptable protonized or protonated organic base, which active principle is in solution or heterogeneously distributed throughout a hydroalcoholic gel in which it is insoluble, and a method of preparing the same. Further objects of the invention will be obvious to one skilled in the art and still others will become apparent upon reading the following specification and claims.

SUMMARY OF THE INVENTION

The invention, then, comprises the following aspects, inter alia, singly or in combination:

A heterogeneous topical composition which can be used as a slenderizing agent or in the treatment of cellulitis, which comprises, as active principle, a topically-acceptable organic salt of caffeine carboxylic acid, said active principle being present in solution and/or the form of microparticles or microgranules in suspension within a hydroalcoholic gel; such a composition wherein the organic salt of caffeine carboxylic acid is in accord with Formula I; such a composition which can be used as slenderizer or in the treatment of cellulitis, which comprises, as active principle, a topically-acceptable caffeine carboxylate, said active principle being present in the form of microgranules or microparticles, having a diameter of about 0.2 to 2 millimeters, which are heterogeneously-distributed and suspended in a hydroalcoholic gel in which they are insoluble, said caffeine carboxylate being selected from the group consisting of 3-nicotinol caffeine carboxylate, triethanolamine caffeine carboxylate, β-dimethylaminoethanol, β-pyrrolidinoethanol, and creatinol caffeine carboxylate; such a composition wherein the caffeine carboxylate is 3-nicotinol caffeine carboxylate; such a composition wherein the caffeine carboxylate is triethanolamine caffeine carboxylate; such a composition wherein the caffeine carboxylate is β-dimethylaminoethanol; such a composition wherein the caffeine carboxylate is β-pyrrolidinoethanol; such a composition wherein the caffeine carboxylate is creatinol caffeine carboxylate; such a composition wherein the microgranules or microparticles have a diameter between about 0.4 and 1 millimeter; such a composition wherein the microgranules or microparticles are present in an amount between about 0.5 and 20 percent by weight of the total composition; such a composition wherein the microgranules or microparticles are present in an amount between about 1 and 10 percent by weight of the total composition; such a composition wherein the individual particles comprising the microgranules or microparticles are of an average size between about 5 and 20 microns in diameter; such a composition wherein the individual particles comprising the microparticles or microgranules are of an average size between about 5 and 15 microns in diameter; such a composition wherein the composition also contains Vitamin E or a derivative thereof and/or caffeine and/or a further derivative thereof.

Moreover, a method of preparing microparticles or microgranules containing as active principle a topically-acceptable organic salt of caffeine carboxylic acid, comprising the following steps, steps a) and c) being optional:

a) a solid inert binder support is micronized until scales of an average size less than 50 microns are obtained, b) particles impregnated with active principle or particles of the active principle itself are micronized until particles of an average size less than 50 microns are obtained, c) the scales when obtained in step a) are mixed with the particles obtained in step b), and d) a wetting agent is added; the product from step b) or c) is agglomerated and the agglomerated product is dried to produce a powder which, after drying, is screened to form microgranules or microparticles of about 0.2 to 2 millimeters in diameter; such a method wherein the microgranules or microparticles are heterogeneously mixed into a hydroalcoholic gel in which they are insoluble; such a method wherein the microgranules or microparticles are mixed into the gel in an amount of about 0.5 to 20 percent by weight of the total composition, and such a method wherein the microgranules or microparticles are mixed into the gel in an amount of about 1 to 10 percent by weight of the total composition.

Further, a method of preparing a hydroalcoholic gel comprising microgranules containing as active principle a salt of caffeine carboxylic acid with a cosmetologically-acceptable organic base, wherein preparation of the microgranules comprises the following steps:

a) an inert binder support is micronized until lamellae of an average size of less than 50 μm are obtained;

b) particles impregnated with the active principle are micronized until particles of an average size of less than 50 μm are obtained;

c) the lamellae obtained in Step a) are mixed with the particles obtained in Step b);

d) an alcohol is added as wetting agent, the product dried, and the powder obtained is screened to form microgranules of a diameter between about 0.2 and 2 mm; and e) the powder is incorporated into a hydroalcoholic gel.

The hydroalcoholic gel is preferably a hydroethanolic gel, the term "cosmetically-acceptable" can replace "topically-acceptable", and the Vitamin E derivative when present is preferably a Vitamin E alkanoic ester such as Vitamin E acetate or palmitate.

DETAILED DESCRIPTION OF THE INVENTION

The preparation of the new active principle used in the compositions of the present invention and the compositions themselves is illustrated by the Preparations and Examples which follow, which are given by way of illustration only and are not to be construed as limiting.

PREPARATION OF ACTIVE PRINCIPLE

Preparation 1

Preparation of 3-nicotinol caffeine carboxylate

This chemical compound can be obtained by the following procedure: One (1) mole of 3-nicotinol (109.1) grams is added to one (1) mole of caffeine carboxylic acid (238.2 grams) which is diluted in three (3) liters of water. The reaction mixture is heated until solids have dissolved. The solution is concentrated to dryness and there is quantitatively recovered the desired product having the formula

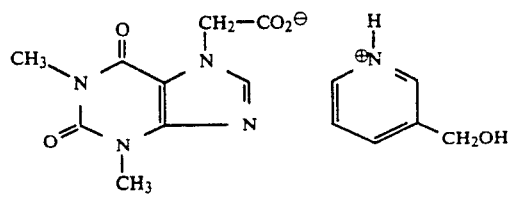

General formula: $C_{15}H_{17}O_5N_5$ MW = 347.34
Physicochemical characteristics:
White crystals. Melting point: 145° C.
Elementary Analysis (Batch MEI25)

|  | C % | H % | N % |
|---|---|---|---|
| Calculated | 51.87 | 4.95 | 20.16 |
| Found | 51.90 | 4.88 | 20.15 |
| Solubility: 2% in water. | | | |

This product, and others which follow, can also be obtained in industrial quantities by spraying from an aqueous solution. It is to be noted that, to avoid entrainment of vapor of the 3-nicotinol, it is in such case necessary to operate under reduced pressure and within a narrow temperature range.

The following products were prepared in a manner similar to that described in Preparation 1.

Preparation 2

Triethanolamine caffeine carboxylate

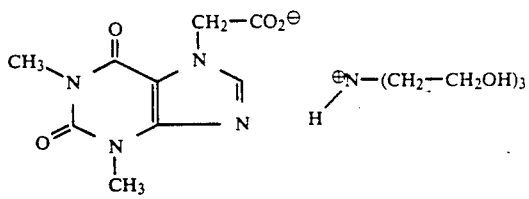

General formula: $C_{15}H_{25}N_5O_7$ MW = 387.4
Physicochemical characteristics:
White crystals. Melting point: 125° C.
Elementary Analysis (Batch F116)

|  | C % | H % | N % |
|---|---|---|---|
| Calculated | 46.51 | 6.50 | 18.08 |
| Found | 46.38 | 5.85 | 19.24 |
| Solubility: 0.4% in water. | | | |

Preparation 3

β-Dimethylaminoethanol caffeine carboxylate

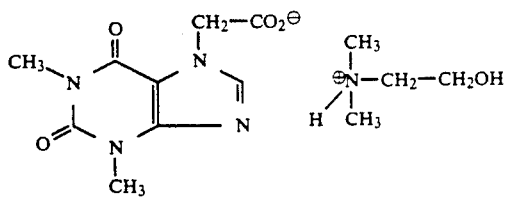

General formula: $C_{13}H_{21}N_5O_5$ MW = 327.34

Physicochemical characteristics:
White crystals. Melting point: 120° C.
Elementary Analysis (Batch F117)

| | C % | H % | N % |
|---|---|---|---|
| Calculated | 47.70 | 6.47 | 21.40 |
| Found | 47.40 | 6.03 | 21.52 |

Solubility: 0.8% in water.

Preparation 4

β-Pyrrolidinoethanol caffeine carboxylate

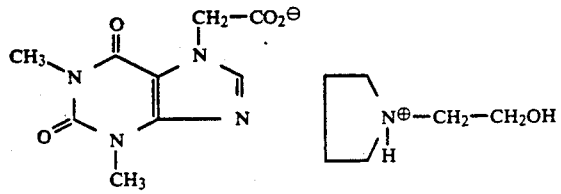

General formula: $C_{15}H_{23}N_5O_5$ MW = 353.38
Physicochemical characteristics:
White crystals. Melting point: 126° C.
Elementary Analysis (Batch F118)

| | C % | H % | N % |
|---|---|---|---|
| Calculated | 50.98 | 6.56 | 19.82 |
| Found | 51.01 | 6.50 | 20.02 |

Solubility: 0.5% in water.

Preparation 5

Creatinol caffeine carboxylate

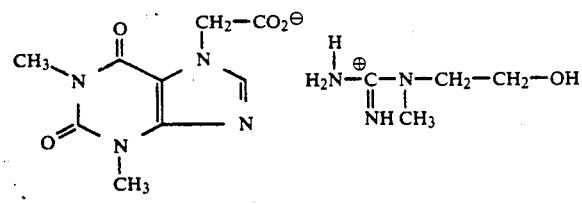

General formula: $C_{13}H_{21}N_7O_5$ MW = 355.36
Physicochemical characteristics:
White crystals. Melting point: 190° C.
Elementary Analysis (Batch AXXI 53)

| | C % | H % | N % |
|---|---|---|---|
| Calculated | 43.94 | 5.95 | 27.59 |
| Found | 44.68 | 5.70 | 27.83 |

Solubility: 12% in water.

Additional Preparations

Numerous additional salts of caffeine carboxylic acid with further cosmetologically-acceptable protonized or protonated organic bases are prepared in the same manner as given in the foregoing Preparations, as will be apparent to one skilled in the art.

Formulations of the Invention

According to the present invention, heterogeneous galenic preparations for cosmetic use contain as active principle a caffeine carboxylate of general formula I, whether or not combined with Vitamin E or caffeine or a derivative of either or both.

The active principle is released progressively and in prolonged fashion upon topical application of a formulation of the invention.

This prolonged release is preferably obtained by the preparation of heterogeneous particles or granules comprising at least two solid phases.

The first phase comprises a thermoplastic inert binder support and the second phase comprises particles impregnated with active principle. The method of preparing such formulations entails the following steps:

1. The first phase is micronized until obtaining lamellae of an average size of less than 50μm.
2. The charge particles impregnated with active principle are micronized until obtaining particles of an average size of less than 50 μm.
3. The lamellae obtained in Step 1 are mixed with the particles obtained in Step 2.
4. The ethanol, or other cosmetologically-acceptable lower-alkanol or other alcohol, is added as wetting agent. After drying and aeration, a powder is obtained which is calibrated by screening in order to obtain a particle size of between about 0.2 and 2 mm.
5. Thereafter, the thus-produced microgranules or microparticles are heterogeneously mixed into a hydroalcoholic gel in which they are insoluble, the microgranules or microparticles being mixed into the gel in an amount of about 0.5 to 20 percent by weight of the total composition, preferably in an amount of about 1 to 10 percent by weight of the total composition.

The thus-prepared heterogeneous particles charged with microgranulated active principle in accord with the present invention are active caffeine-protonated organic base-carboxylate principles for slenderizing purposes and useful in the treatment of cellulite, preferably 3-nicotinol caffeine carboxylate, triethanolamine caffeine carboxylate, β-dimethylaminoethanol caffeine carboxylate, β-pyrrolidinoethanol caffeine carboxylate, or creatinol caffeine carboxylate, possibly combined with a vitamin and more particularly Vitamin E and/or a derivative thereof, or a xanthinic derivative and more particularly caffeine or another derivative thereof.

The formulations contain about 0.5 to 20% W/W of microparticles or microgranules charged with active principle in a suitable base containing cosmetic excipients known to one skilled in the art, which base may also contain other active agents in accordance with the invention. The amount of active caffeine carboxylate itself in the particle or granule formulations is preferably between about 5 and about 50 percent by weight.

By way of non-limitative Examples there are provided representative specific formulations of the microparticles or microgranules which can be present in slenderizing hydroalcoholic gels according to the invention.

| | % by weight |
|---|---|
| Example 1 | |
| 3-nicotinol caffeine carboxylate | 5 to 20 |
| Starch | 20 to 30 |
| Ethylcellulose | 5 to 20 |
| Other excipients | qsp 100 |
| Example 2 | |
| Triethanolamine caffeine carboxylate | 10 to 40 |
| Starch | 20 to 30 |
| Other excipients | qsp 100 |

-continued

| | % by weight |
|---|---|
| Example 3 | |
| β-Dimethylaminoethanol caffeine carboxylate | 10 to 40 |
| Caffeine | 5 to 10 |
| Vitamin E, its palmitate or acetate | 10 to 20 |
| Excipients including binder | qsp 100 |
| Example 4 | |
| β-Pyrrolidinoethanol caffeine carboxylate | 10 to 40 |
| Vitamin E | 5 to 20 |
| Excipients including binder | qsp 100 |
| Example 5 | |
| Creatinol caffeine carboxylate | 5 to 30 |
| Starch | 5 to 20 |
| Other excipients including binder | qsp 100 |

EXAMPLE 6

Additional Formulations

Numerous additional microparticles and microgranules containing additional salts of caffeine carboxylic acid with further cosmetologically-acceptable protonized or protonated organic bases are prepared in the same manner as given in the foregoing Examples, with numerous variations in the particular caffeine carboxylate and excipients, including binders, being available and being readily apparent to one skilled in the art.

EXAMPLE 7

Solution Formulations

Solutions of salts of caffeine carboxylic acid with cosmetologically-acceptable organic bases, such as those disclosed in the foregoing Preparations and shown in the foregoing Examples, may be made by dissolving the particular selected salt in water or in an alcohol, e.g., ethyl alcohol, or in an aqueous medium comprising both water and an alcohol, e.g., ethanol, or in a polyethyleneglycol, or in an aqueous medium comprising polyethyleneglycol, and these may be applied topically in the usual manner for slenderizing and the elimination of cellulitis. However, although the active ingredients of the present invention are characterized by a superior and advantageous rate of transcutaneous passage, the prolonged action and effect thereof is not attained with solutions of the caffeine carboxylate, but only when the carboxylate is administered in the form of microparticles or microgranules homogeneously distributed in a hydroalcoholic gel, e.g., a gel form comprising water and an alcohol, as further set forth herein and specifically exemplified by Example 8 hereof.

The formulations in accord with the present invention are tolerated well. They incorporate soft microparticles or microgranules which do not involve any inorganic agent which might be considered a foreign body. According to the present invention, the formulations prepared, taking into account the presence of an active principle which is a caffeine carboxylate of an organic amine base which is characterized by a superior and advantageous rate of transcutaneous passage, have excellent slenderizing properties and have been found to be very effective in the treatment of cellulite.

In the last step, the microparticles and/or microgranules were treated with a wetting agent, the wetted mass agglomerated into larger particles and/or granules, the particles or granules dried to form a powder, and the powder sieved or screened to provide microgranules or microparticles having an average particle size of about 0.2 to 2 millimeters, preferably about 0.4 to 1 millimeter, in diameter.

Finally, the caffeine carboxylate microparticles or microgranules are combined into and heterogeneously distributed in the hydroalcoholic gel by simple careful introduction and admixture into the gel composition, according to the skill of the art. The gel formulations of the invention contain about 0.5 to 20% w/w, preferably 1 to 10% w/w, of microgranules charged with active principle or microparticles of pure active principle itself in a suitable base comprising cosmetic excipients in the form of a hydroalcoholic gel, usually of a transparent or preferably translucent nature, attained in a manner known to one skilled in the art. The base is, however, selected so that the particles are totally or essentially insoluble therein. A representative final gel composition having the following illustrative ingredients and proportions follows:

FINAL HYDROALCOHOLIC GEL COMPOSITION

EXAMPLE 8

| | |
|---|---|
| Algae extract (agar) | 0 to 5% by weight |
| 95° ethanol (or other non-toxic alcoholic compound) | 10 to 30% (makes a hydroethanolic gel) |
| Carboxyvinyl polymer (or other polymeric support) | 0.3 to 6%, preferably 0.3 to 1% |
| Triethanolamine | 3 to 10% |
| Microgranules or microparticles according to any of Examples 1 to 6 | 0.5 to 20% (preferably 1 to 10%) |
| Softened (demineralized) water | qsp 100% w/w |

The insoluble or nearly-insoluble microgranules or microparticles are randomly and heterogeneously distributed throughout the translucent gel by stirring thereinto. The product is used by applying it to the area to be slenderized, or to the area in which cellulitis is to be reduced or eliminated, and rubbing it in, according to conventional practice in the art.

VARIATIONS IN COMPOSITIONS AND RANGES

A. Inert Binder Support

Examples of other suitable materials are polymeric materials and especially thermoplastic polymeric materials such as ethylcellulose, ethylhydroxycellulose, hydroxypropylcellulose, carboxymethylcelluloses, and despolyvinylpyrrolidones.

B. Range of Starting Microgranule or Microparticle Ingredient Diameters

Less than 50 microns, preferably 5 to 20 microns, advantageously 5–15 microns. C. Range of Final Microgranule or Microparticle Diameters Average particle diameter of about 0.2 to 2 millimeters, preferably about 0.4 to 1 millimeter.

D. Wetting agent

A lower-alcohol, preferably a lower-alkanol such as ethanol, methanol, propanol, or isopropanol, ethanol being preferred.

E. The Gel Formulation

The formulations contain about 0.5 to 20% w/w of microgranules or microparticles on a basis of the total composition including the hydroalcoholic gel, and preferably contain about 1 to 10% w/w of microgranules or microparticles on a basis of the total composition including the hydroalcoholic gel.

As already stated, the heterogeneous caffeine carboxylate gel formulations of the present invention are tolerated well. They place in action soft microgranules or microparticles which do not involve the intervention of any inorganic agent which could be considered a foreign body.

Also, as already stated, and in accord with the present invention, the formulations prepared on a basis of the presence, as active principle, of a caffeine metal carboxylate, have excellent and long-acting "lipolytic" properties and have therefore proven very effective in slenderizing programs and in the treatment of cellulitis.

In conclusion, from the foregoing, it is apparent that the present invention provides novel topical compositions useful for slenderizing and/or in the treatment of cellulitis, involving the local or topical application thereof, in which novel topical compositions a topically or cosmetically-acceptable caffeine carboxylate with a cosmetologically-acceptable protonated organic or amine base, is present, preferably in the form of soft heterogeneously-distributed microgranules or microparticles in a topically-acceptable hydroalcoholic gel carrier or diluent, in which it is insoluble, all having the foregoing enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

We claim:

1. Heterogeneous cosmetic composition which can be used as a slenderizing agent or in the treatment of cellulitis, which comprises, an active principle selected from the group consisting of 3-nicotinol caffeine carboxylate, triethanolamine caffeine carboxylate, -pyrrolidinoethanol caffeine carboxylate and creationol caffeine carboxylate, said active principle being present in the form of microgranules or microparticles, in an amount between about 0.5 and 20% by weight of the total composition, and which microgranules or microparticles are heterogeneously distributed and suspended in a gel comprising water and a non-toxic alcohol in which they are insoluble.

2. A composition according to claim 1, wherein the caffeine carboxylate is 3-nicotinol caffeine carboxylate.

3. A composition according to claim 1, wherein the caffeine carboxylate is triethanolamine caffeine carboxylate.

4. A composition according to claim 1, wherein the caffeine carboxylate is β-dimethylaminoethanol.

5. A composition according to claim 1, wherein the caffeine carboxylate is β-pyrrolidinoethanol.

6. A composition according to claim 1, wherein the caffeine carboxylate is creatinol caffeine carboxylate.

7. Composition of claim 3 wherein the microgranules or microparticles have a diameter between about 0.4 and 1 millimeter.

8. Composition of claim 1 wherein the microgranules or microparticles are present in an amount between about 1 and 10 percent by weight of the total composition.

9. Composition of claim 1 wherein the individual particles comprising the microgranules or microparticles are of an average size between about 5 and 20 microns in diameter.

10. Composition of claim 1 wherein the individual particles comprising the microparticles or microgranules are of an average size between about 5 and 15 microns in diameter.

11. A composition according to claim 1 wherein the composition also contains vitamin E.

12. A method of preparing microparticles or microgranules containing as active principle a topically-acceptable organic salt of caffeine carboxylic acid, comprising the following steps, steps a) and c) being optional:
    a) a solid inert binder support is micronized until scales of an average size less than 50 microns are obtained,
    b) particles impregnated with active principle or particles of the active principle itself are micronized until particles of an average size less than 50 microns are obtained,
    c) the scales when obtained in step a) are mixed with the particles obtained in step b)
    d) a wetting agent is added; the product from step b) or c) is agglomerated and the agglomerated product is dried to produce a powder which, after drying, is screened to form microgranules or microparticles of about 0.2 to 2 millimeters in diameter.

13. Method of claim 12 wherein the microgranules or microparticles are heterogeneously mixed into a hydroalcoholic gel in which they are insoluble.

14. Method of claim 13 wherein the microgranules or microparticles are mixed into the gel in an amount of about 0.5 to 20 percent by weight of the total composition.

15. Method of claim 13 wherein the microgranules or microparticles are mixed into the gel in an amount of about 1 to 10 percent by weight of the total composition.

16. A method of preparing a hydroalcoholic gel comprising microgranules containing as active principle a salt of caffeine carboxylic acid with a cosmetologically-acceptable organic base, wherein preparation of the microgranules comprises the following steps:
    a) an inert binder support is micronized until lamellae of an average size of less than 50 μm are obtained;
    b) particles impregnated with the active principle are micronized until particles of an average size of less than 50 μm are obtained;
    c) the lamellae obtained in Step a) are mixed with the particles obtained in Step b);
    d) an alcohol is added as wetting agent, the product dried, and the powder obtained is screened to form microgranules of a diameter between about 0.2 and 2 mm; and
    e) the powder is incorporated into a hydroalcoholic gel.

* * * * *

UNITED STATES PATENT AND TRADEMARK OFFICE
CERTIFICATE OF CORRECTION

PATENT NO. : 5,030,451

DATED : July 9, 1991

INVENTOR(S) : Marie-Thérése Trebosc, Gilbert Mouzin and Henri Cousse

It is certified that error appears in the above-identified patent and that said Letters Patent is hereby corrected as shown below:   Title Page, [54], and Col. 1, line 2, in both instances correct in the second line of the title; "CAFEINE" should read -- CAFFEINE --
Col. 9, line 47; "carboxylate,-pyrrolidinoethanol" should read
 -- carboxylate, β-dimethylaminoethanol caffeine carboxylate,
    β-pyrrolidinoethanol --

Col. 10, line 1; "claim 3" should read -- claim 1 --
Col. 10, line 20; "acid, com-" should read -- acid, selected from the group consisting of 3-nicotinol caffeine carboxylate, triethanolamine caffeine carboxylate, β-dimethylaminoethanol caffeine carboxylate, β-pyrrolidinoethanol caffeine carboxylate and creatinol caffeine carboxylate, com- --

Col. 10, line 51; "base, wherein" should read -- base, selected from the group consisting of 3-nicotinol caffeine carboxylate, triethanolamine caffeine carboxylate, β-dimethylaminoethanol caffeine carboxylate, β-pyrrolidinoethanol caffeine carboxylate and creatinol caffeine carboxylate, wherein --

Col. 10, lines 64&65; "a hydroalcoholic gel." should read -- a gel comprising water and a non-toxic alcohol in which the microgranules are insoluble --

Signed and Sealed this

Second Day of February, 1993

*Attest:*

STEPHEN G. KUNIN

*Attesting Officer*           *Acting Commissioner of Patents and Trademarks*